(12) United States Patent
Walker

(10) Patent No.: US 8,292,965 B2
(45) Date of Patent: Oct. 23, 2012

(54) KNEE JOINT WITH A RAMP

(75) Inventor: Peter Stanley Walker, New York, NY (US)

(73) Assignee: New York University, New York, NY (US)

(*) Notice: Subject to any disclaimer, the term of this patent is extended or adjusted under 35 U.S.C. 154(b) by 209 days.

(21) Appl. No.: 12/069,414

(22) Filed: Feb. 11, 2008

(65) Prior Publication Data
US 2009/0204221 A1 Aug. 13, 2009

(51) Int. Cl.
*A61F 2/38* (2006.01)
(52) U.S. Cl. .................. 623/20.27; 623/20.31
(58) Field of Classification Search .......... 623/20.14, 623/20.29, 20.15–20.17, 20.21–20.28, 20.31–20.36
See application file for complete search history.

(56) References Cited

U.S. PATENT DOCUMENTS

| | | | | |
|---|---|---|---|---|
| 3,798,679 | A | * | 3/1974 | Ewald ............... 623/20.31 |
| 3,816,855 | A | * | 6/1974 | Saleh ............... 623/20.31 |
| RE29,757 | E | * | 9/1978 | Helfet ............... 623/20.31 |
| 4,634,444 | A | * | 1/1987 | Noiles ............... 623/20.27 |
| 5,133,758 | A | * | 7/1992 | Hollister ............ 623/20.31 |
| 5,137,536 | A | * | 8/1992 | Koshino ............. 623/20.34 |
| 5,330,533 | A | | 7/1994 | Walker |
| 5,702,460 | A | | 12/1997 | Carls et al. |
| 5,702,466 | A | | 12/1997 | Pappas et al. |
| 6,039,764 | A | | 3/2000 | Pottenger et al. |
| 6,074,425 | A | | 6/2000 | Pappas |
| 6,117,175 | A | | 9/2000 | Bosredon |
| 6,123,729 | A | | 9/2000 | Insall et al. |
| 6,126,693 | A | | 10/2000 | O'Neil et al. |
| 6,152,960 | A | | 11/2000 | Pappas |
| 6,165,222 | A | | 12/2000 | Hoeppner et al. |
| 6,203,576 | B1 | | 3/2001 | Afriat et al. |
| 6,206,926 | B1 | | 3/2001 | Pappas |
| 6,217,619 | B1 | | 4/2001 | Keller |
| 6,235,060 | B1 | | 5/2001 | Kubein-Meesenburg et al. |
| 6,264,697 | B1 | * | 7/2001 | Walker ............... 623/20.27 |
| 6,299,645 | B1 | | 10/2001 | Ogden |
| 6,325,828 | B1 | | 12/2001 | Dennis et al. |
| 6,406,497 | B2 | | 6/2002 | Takei |
| 6,413,279 | B1 | * | 7/2002 | Metzger et al. ........ 623/20.29 |
| 6,416,552 | B1 | | 7/2002 | Hoeppner et al. |
| 6,443,991 | B1 | | 9/2002 | Running |
| 6,527,807 | B1 | | 3/2003 | O'Neil et al. |

(Continued)

FOREIGN PATENT DOCUMENTS

WO WO 92/08424 * 5/1992

*Primary Examiner* — William H. Matthews
*Assistant Examiner* — Marcia Hoffman
(74) *Attorney, Agent, or Firm* — Kelley Drye & Warren LLP

(57) ABSTRACT

An artificial knee joint is described that includes a femoral component with a specially shaped bearing surface and a tibial component, whose surface interacts with the femoral surfaces. The interaction provides for the required motion and stability characteristics. The interaction between the femoral and tibial surfaces is such that as the knee is flexed to maximum, the femoral component moves posteriorly on the tibial surface, by an amount similar to that in the anatomic knee. The opposite motion, roll forward of the femur from a fully flexed to a more extended position, is accomplished by varying the outward radii of the lateral and medial femoral bearing surfaces, together with a ramp on the postero-lateral and postero-medial regions of the tibial surfaces.

11 Claims, 6 Drawing Sheets

U.S. PATENT DOCUMENTS

| | | | |
|---|---|---|---|
| 6,540,786 B2 | 4/2003 | Chibrac et al. | |
| 6,540,787 B2 * | 4/2003 | Biegun et al. | 623/20.31 |
| 6,589,283 B1 | 7/2003 | Metzger et al. | |
| 6,616,696 B1 | 9/2003 | Merchant | |
| 6,770,097 B2 | 8/2004 | Leclercq | |
| 6,846,329 B2 | 1/2005 | McMinn | |
| 6,887,276 B2 | 5/2005 | Gerbec et al. | |
| 6,893,467 B1 | 5/2005 | Bercovy | |
| 6,902,582 B2 | 6/2005 | Kubein-Meesenburg et al. | |
| 6,962,607 B2 | 11/2005 | Gundlapalli et al. | |
| 6,986,791 B1 | 1/2006 | Metzger | |
| 7,025,788 B2 | 4/2006 | Metzger et al. | |
| 7,264,635 B2 | 9/2007 | Suguro et al. | |
| 7,326,252 B2 | 2/2008 | Otto et al. | |
| 7,354,454 B2 | 4/2008 | Stack et al. | |
| 7,364,590 B2 | 4/2008 | Siebel | |
| 7,413,577 B1 | 8/2008 | Servidio | |
| 7,497,874 B1 | 3/2009 | Metzger et al. | |
| 7,625,407 B2 * | 12/2009 | Akizuki et al. | 623/20.32 |
| 2002/0010512 A1 | 1/2002 | Takei | |
| 2002/0022889 A1 | 2/2002 | Chibrac et al. | |
| 2002/0120340 A1 | 8/2002 | Metzger et al. | |
| 2004/0143339 A1 | 7/2004 | Axelson et al. | |
| 2004/0186582 A1 | 9/2004 | Yasuda et al. | |
| 2004/0243244 A1 | 12/2004 | Otto et al. | |
| 2005/0055102 A1 | 3/2005 | Tornier et al. | |
| 2005/0102032 A1 | 5/2005 | Beynnon et al. | |
| 2005/0209701 A1 | 9/2005 | Suguro et al. | |
| 2006/0142867 A1 | 6/2006 | Metzger et al. | |
| 2007/0135926 A1 * | 6/2007 | Walker | 623/20.31 |
| 2008/0140212 A1 | 6/2008 | Metzger et al. | |
| 2009/0043396 A1 | 2/2009 | Komistek | |

* cited by examiner

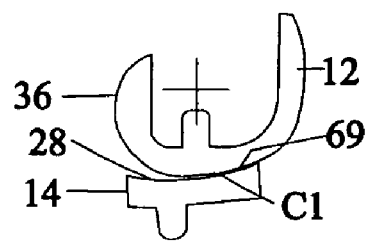 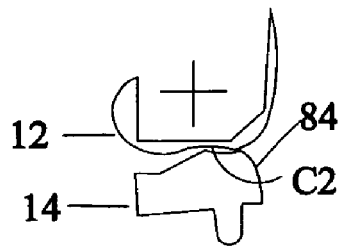 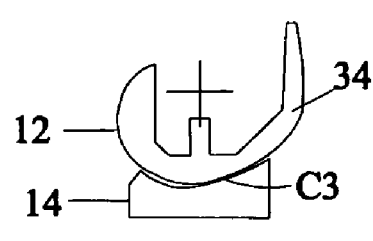
FIG. 9a  FIG. 9b  FIG. 9c
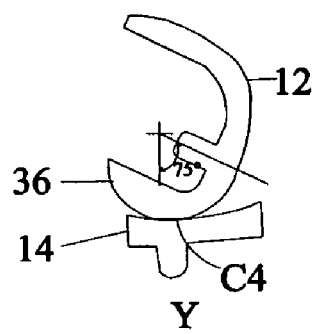 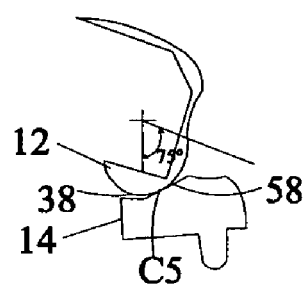 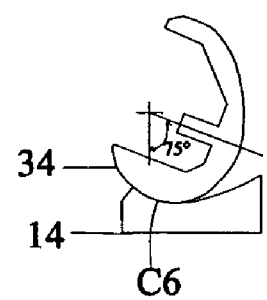
FIG. 9d  FIG. 9e  FIG. 9f
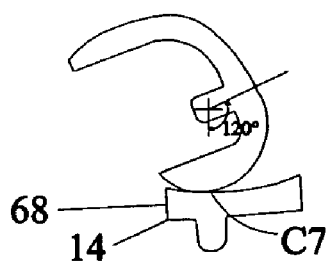 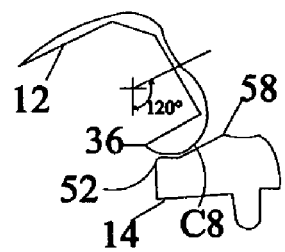 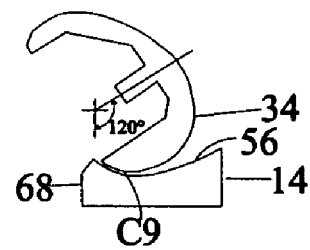
FIG. 9g  FIG. 9h  FIG. 9i

KNEE JOINT WITH A RAMP

FIELD OF THE INVENTION

The present invention relates to total knee prostheses and more specifically to a knee joint having femoral components and a tibial component that are specifically shaped for posterior cruciate retention and substituting.

BACKGROUND OF THE INVENTION

The large majority of the total knees implanted today are either of the posterior cruciate retaining (CR) or posterior stabilized (PS) types. These have both functioned well clinically, but a number of disadvantages remain. Due to variations in surgical techniques and between patients, when using the CR type of total knee, it has been difficult to obtain an optimal tightness of the posterior cruciate ligament (PCL) throughout flexion, resulting in variable rollback patterns.

For the PS, considerably extra bone needs to be resected from the center of the femur to accommodate the intercondylar housing of the femoral component, for the cam and post mechanism. Damage can sometimes occur to the plastic post in the long term, anteriorly due to impacts at full extension, and posteriorly due to high flexion loading. In addition, in many PS designs, there is a tendency for overconstraint in rotation due to the dishing of the tibial bearing surfaces, in combination with the construct of the cam-post.

A disadvantage common to both CR and PS types, although more pronounced with CR designs due to their shallower tibial bearing surfaces, is a paradoxical motion in which the femur slides forwards on the tibial surface during the first half of the flexion range, rather than backwards which is the required motion. Also, uneven or jerky motion occurs in many cases. Artificial knees have included configurations that accommodate medial pivotal rotation to resemble the anatomical motion in the anatomic knee. However, these configurations may not incorporate a mechanism for achieving lateral rollback in flexion in combination with a relatively immobile medial side, or do not provide sufficient laxity about the neutral path of motion.

A knee joint system is needed that has a femoral component and a tibial component that have specific contours and surfaces that guide the knee joint into an average anatomic neutral path of motion during flexion-extension, while having sufficient laxity about that neutral path to accommodate different individuals and activities; and that can be used as both a CR and PS types.

SUMMARY OF THE INVENTION

A knee joint for prosthesis for guiding the motion and preventing paradoxical motions is described that includes a tibial component having a lateral bearing surface and a medial bearing surface that are separated by a ramp. The medial bearing surface has a smaller sagittal plane radius of curvature than the lateral bearing surface. The medial bearing surface includes a raised pad in an anterior medial bearing surface The knee joint includes a femoral component that includes a lateral condyle and medial condyle that are separated by a groove. The groove interfaces with the ramp of the tibial component to produce a posterior movement during flexion of the joint. The ramp with a plurality of smooth edges has a height that decreases gradually from an anterior portion to a posterior portion of the tibial component to guide the femoral component to displace posteriorly during flexion and displace anteriorly during extension.

The deeper medial tibial surface and the shallow lateral surface of the tibia results in most of the posterior displacement of the femur occurring laterally with only a small displacement medially. The femoral component includes a recess located antero-medially, which interfaces with the said tibia pad. The antero-medial recess-pad feature limits anterior femoral displacement in early flexion. This combined ramp system guides the motion of the knee into an anatomic motion pattern consisting of external femoral rotation of the femur about a medial axis on the tibia, as flexion proceeds. The femoral component also includes a patella flange in a proximal-anterior portion.

When the system is used as a CR device, the PCL provides some of the motion guidance. When used as a PS device, the features of the ramp guide the motion. Sufficient laxity about the neutral path allows for variations of motion. One of the benefits of the system is that anterior sliding of the femur on the tibia from approximately 0-60° flexion (paradoxical motion) is minimized due to the medial femoral recess as it interfaces with the antero-medial tibial pad feature.

The femoral component is advantageously used in PS type of knee prosthesis. In one more embodiment of the present invention, the femoral component is used for CR type of knee prosthesis with the similar tibial component. The two femoral components are identical except for a central recess to provide access to the PCL in the CR version of the femoral component.

Large contact surface areas between the femoral and tibial components, especially on the medial side, which is highly loaded than the lateral side, minimize wear and deformation of the polyethylene surfaces. Additionally, smooth contours around the central tibial ramp avoid stress concentrations which could result in damage to the plastic. Minimal bone resection is required from the central part of the femur for installation of the femoral component.

The same tibial component can be advantageously used with either the PS or CR femoral component. For application to a symmetric shape of tibial baseplate, which is commonly used, the tibial bearing surface can have 5° of external rotation built in, providing an anatomic position of the femur on the tibia at 0° flexion.

BRIEF DESCRIPTION OF THE DRAWINGS

FIGS. 9a-9c show nature of contact between the femoral component and the tibial component at 0° flexion along planes-A, B and C that pass through a medial portion, a central portion and a lateral portion respectively of the tibial component of the FIG. 1;

FIGS. 9d-9f show nature of contact between the femoral component and the tibial component at 75° flexion along planes-A, B and C that pass through a medial portion, a central portion and a lateral portion respectively of the tibial component of the FIG. 1;

FIGS. 9g-9i show nature of contact between the femoral component and the tibial component at 120° flexion along planes-A, B and C that pass through a medial portion, a central portion and a lateral portion respectively of the tibial component of the FIG. 1;

DETAILED DESCRIPTION OF THE INVENTION

Figure 1:
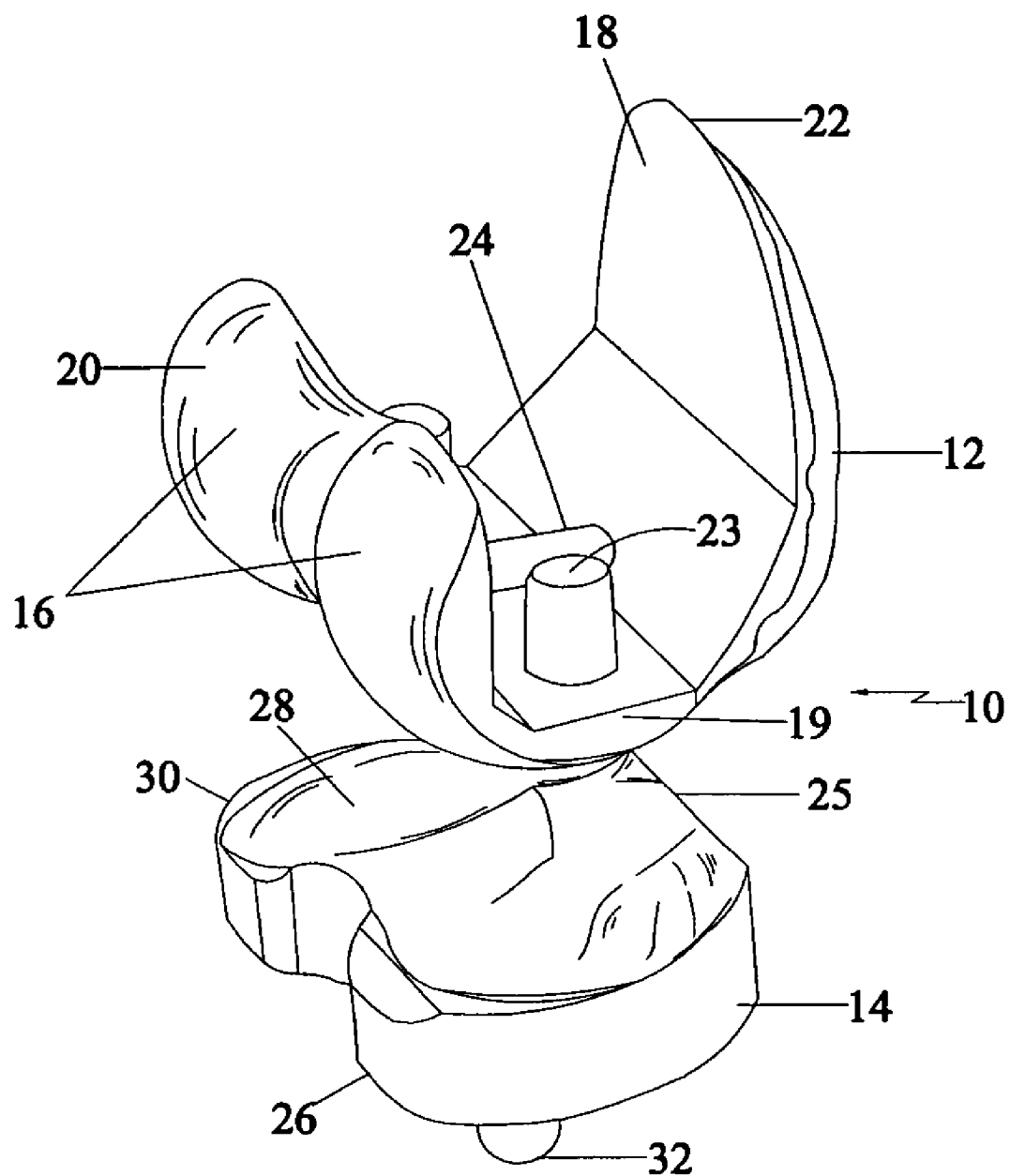
FIG. 1 shows a posterior-medial perspective view of a posterior substituting (PS) femoral component and tibial component in accordance with a preferred embodiment of the present invention.

Referring to FIG. 1, the knee joint 10 in a zero degree flexion in accordance with a preferred embodiment of the present invention is shown. The knee joint 10 of the present invention includes a femoral component 12 and a tibial component 14. Femoral component 12 is preferably connected to a predefined distal end of a femur. The tibial component 14 is preferably connected to a predefined proximal end of a tibia.

The femoral component 12 is a one-piece arcuate construction that includes a pair of convex femoral condyles 16 and a patella flange 18. Condyles 16 and patella flange 18 converge inwardly to meet in the distal portion 19 of the femoral component 12 to form the arcuate shape. The pair of condyles 16 forms a proximal-posterior portion 20 and the patella flange 18 forms an opposed proximal-anterior portion 22. An interior side of distal portion 19 has a pair of pegs 23. The interior side of the distal portion 19 of femoral component 12 includes approximately centrally placed low profile hump 24.

The tibial component 14 is also a one piece construction having a proximal end portion 25 and a distal end portion 26. The proximal end portion 25 includes a receiving surface 28 that is defined by a periphery 30 of the tibial component 14. The distal end portion 26 includes three pegs 32. In this one preferred embodiment, the tibial component 14 is one-piece, however it is understood, that the tibial component 14 can be a bearing component that is fixable into a tibial tray or a base plate.

Figures 2, 3:
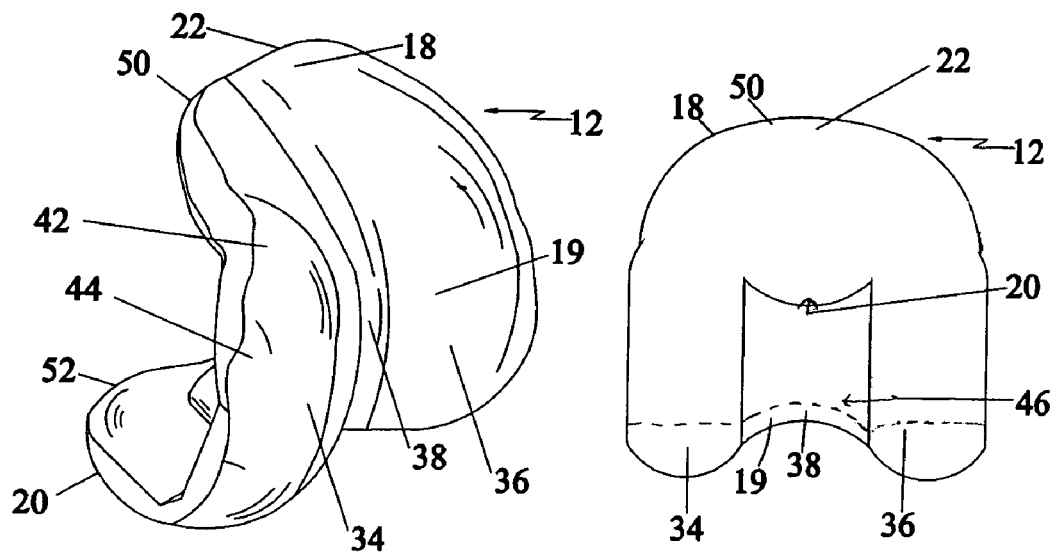
FIG. 2 shows an anterio-medial perspective view of the femoral component of FIG. 1.
FIG. 3 shows a posterior view of the femoral component of FIG. 1.

Referring to FIGS. 2-3, the proximal posterior portion 20 of the femoral component 12 includes medial condyle 34 and a lateral condyle 36. The medial condyle 34 and lateral condyle 36 are separated by an intercondylar groove 38 that runs centrally from the proximal anterior portion 22 to distal portion 19 and continues to a vicinity of proximal posterior portion 20 of the femoral component 12. An anterio-medial side 42 of the medial condyle 34 includes a smooth recess 44.

The patella flange 18 has rounded edges 50 at the proximal-anterior portion 22 of femoral component 12.

The central groove 38 has a depth that varies from the proximal-anterior portion 22 to the proximal-posterior portion 20. The depth of the groove 38 decreases towards proximal-posterior portion 20 of femoral component 12 such that the groove 38 preferably becomes shallow between a portion defined by medial condyle 34 and lateral condyles 36.

Groove 38 is preferably approximately 8 mm-12 mm deep in the distal portion 19 of femoral component 12. Beyond the distal portion 19, in an upward direction of the femoral component, the central height of the groove 38 progressively reduces, such that the groove depth reaches 0-4 mm at proximal posterior portion 20. It is, however, understood that the femoral component 12 is preferably contoured and dimensioned to be a close match to that of the anatomic femur.

Now referring to FIGS. 4-7, the receiving surface 28 of the tibial component 14 has a lateral receiving surface 54 and a medial receiving surface 56, that are separated by a central ramp 58. An anterior medial bearing surface 60 includes a pad 62 that extends up to the anterior edge of the tibial component 14. The tibial component 14 also includes a cutout 66 that is positioned approximately centrally in a posterior portion 68 of the tibial component 14.

The medial bearing surface 56 transits smoothly to ramp 58 and continues smoothly to lateral bearing surface 54. The radii of curvature R1 of the lateral condyle 56 and R2 medial condyle 54 are only 1-4 mm larger than the equivalent radii of curvature of the femoral condyles 34 and 36 in the same section position.

Figure 7:
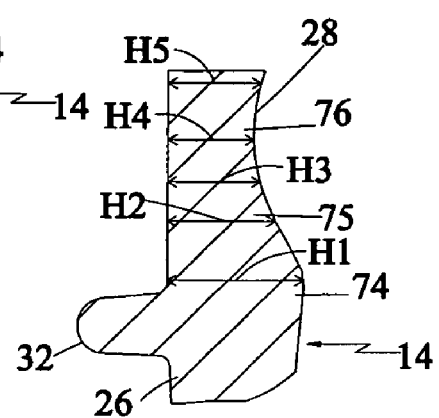
FIG. 7 shows a sectional view taken along a plane-7 of the tibial component that shows construction of a central ramp portion of the tibial component of FIG. 1.
Figure 6:
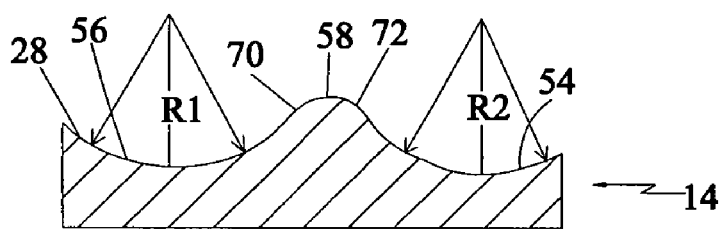
FIG. 6 shows a sectional view taken along a plane-6 of the tibial component that shows construction of a ramp and a tibial bearing surface.

The ramp 58 has a curved medial side 70 and a curved lateral side 72. Surfaces defined by the sides 70 and 72 of the ramp 58 smoothly slope towards the adjacent bearing surfaces. The sides 70 and 72, as shown in FIG. 7 (which is a cross section along line 7-7 of FIG. 5 converge smoothly with the respective bearing surfaces. Ramp 58 has a height that decreases gradually from an anterior portion 74 to a portion 75 and then to posterior portion 76.

H1 indicates a height of the anterior portion 74 of ramp 58. H2 indicates a height of approximately central portion 75 of the ramp 58. H3 indicates a height of a junction of the central portion 75 of the ramp 58. H4 indicates a height of the posterior portion 76 of the ramp 58. H5 indicates a height of posterior portion 68 of tibial component 14. H1 is greater than H2 which is greater than H3. H3 is greater in height than H4. H5 is preferably higher than H4.

The posterior portion 76 of ramp 58 smoothly and gradually meets with the cutout 66 in the posterior portion 68 of tibial component 14. The height and slope of the sides 70 and 72 of ramp 58 advantageously guide femoral component 12 to displace posteriorly during flexion and displace anteriorly during extension. The tibial receiving surface 28 has preferably approximately 5° of external rotation when used with a symmetric baseplate. The distal portion 26 of tibial component is preferably contoured in a predefined smooth shape.

In this preferred embodiment, the distal portion 26 includes three fixation pegs 32, it is, however, understood that many other fixation means known in the art can be used.

Figure 8:
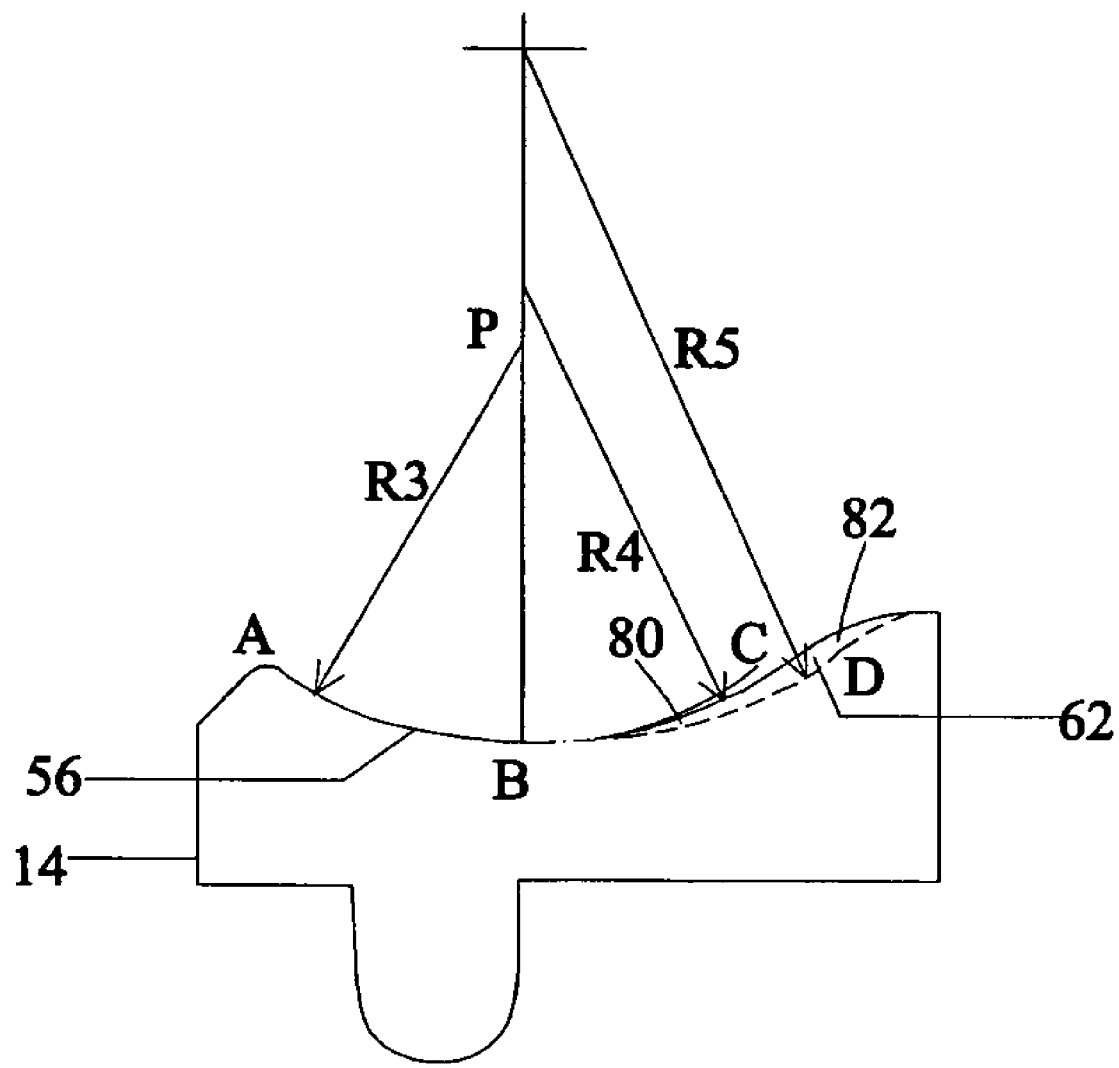
FIG. 8 shows a sectional view taken along a plane-8 passing through a raised pad in an anterior medial bearing surface.

Now referring to FIG. 8, (which is cross section of FIG. 5 at 8-8) the medial bearing surface 56 defined by an arc ABD is shown. Arc AB with a center at point at P has a constant radius that is indicated by R3. The arc AB has been extended to BC with same radius. Arc AB meets with arc BD at point B. The arc BD has a radius which is greater than R5 which matches the distal-anterior radius of the femoral component in extension. However, if this radius was used for tibial surface, in flexion, the femoral radius R3 would readily slide up the slope BD. The pad 62 on the tibial surface is constructed with radius R4, between 0-3 mm greater in radius than R3.

The pad 62 with posterior portion 80 and anterior portion 82 locates within smooth femoral recess 44. The pad 62 is thus in close proximity with the medial femoral condyle 34 in early part of flexion. This limits the anterior sliding of the medial side of the femoral component up the ramp along slope BC. This anterior sliding is also called as paradoxical motion, because in the anatomic knee, anterior sliding does not occur, especially on the medial slide.

The posterior portion 80 of the pad 62 is such that a profile formed by the posterior portion 80 is tangential to the arc BC having radius R3. The pad 62 smoothly joins with the medial bearing surface 56. The pad 62 has a predefined height that is in accordance with the recess 44 on the femoral component 12. Radius R4 of the pad 62 in the posterior portion 80 is preferably 0-3 mm greater than R3, such that it is a close match to the recess 44 of the femoral component 12. R5 is the radius of the femoral component 12 in that region if the recess 44 was not present. It will be appreciated that if the pad and recess were not present, in flexion, radius R3 of the femoral component could easily slide anteriorly up the slope of R5. In this preferred embodiment, femoral component 12 and tibial component 14 are preferably made of metal and a polymer material, respectively. The interface between femoral component 12 and receiving surface 28 is intended to provide the extended wear characteristics that are desirable in a knee replacement.

Figure 4:
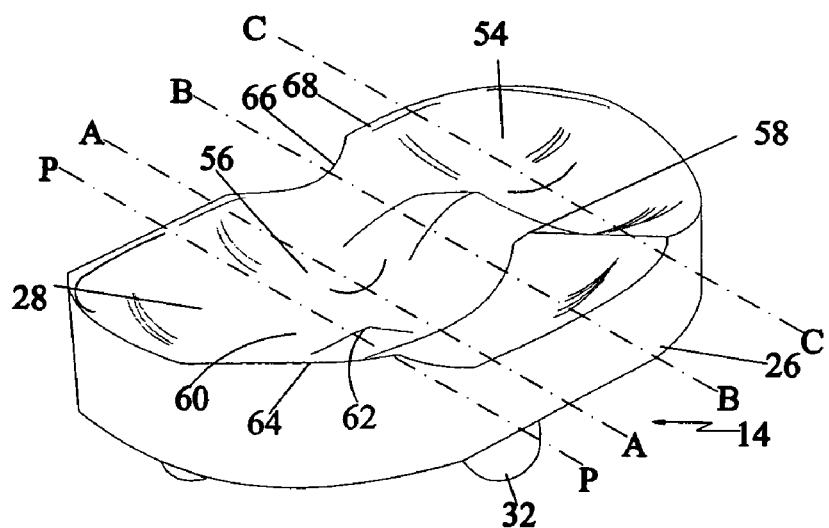
FIG. 4 shows an anterior top perspective view of the tibial component of FIG. 1.
Figure 5:
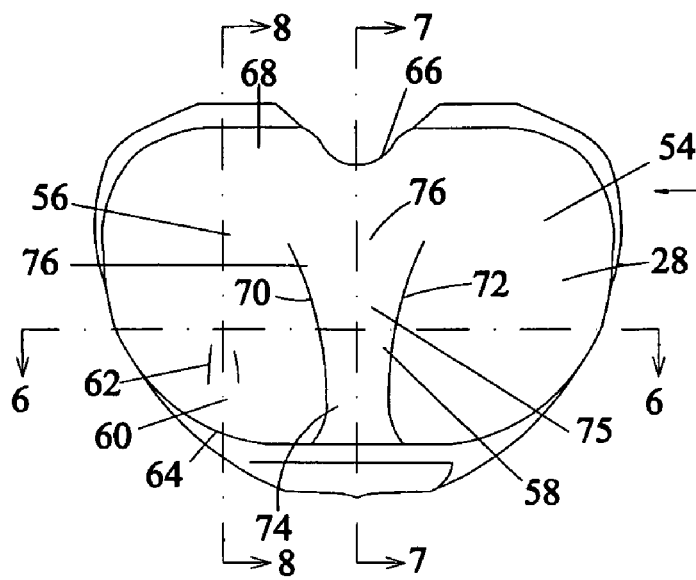
FIG. 5 shows a top view of the tibial component of FIG. 1.

Now referring to in FIGS. 9a-9i, the behavior of condylar and tibial contact at various angles of flexion are described with FIGS. 9a, d and g at cross section AA in FIG. 4; FIG. 9, b, e and h at cross section BB in FIG. 4; and FIGS. 9c, f, and i at cross sections CC in FIG. 4. At 0° flexion (FIG. 9a-c). The contact on the lateral side is towards the anterior of the tibial receiving surface 26 that is indicated by C1 such that an approximately complete conformity exists between the femoral component 12 and tibial component 14, to provide a large area of contact C1. The section through the center at 0° flexion FIG. 9b indicates that the femur will rock on the anterior platform 59 on the tibia if the femur is hyperextended. On the medial side, there is a large area of contact C2 of the interacting femoral and tibial surfaces, a larger area of contact than on the lateral receiving surface.

As the flexion angle increases from zero to 75°, the lateral contact C4 moves posteriorly while the central contact C5 and medial contact C6 also moves posteriorly. By 75° flexion, the central groove 38 of the femoral component 12 interacts with central ramp 58 of the tibial component 14. The contact C6 with the medial bearing surface moves posteriorly at 75° flexion by approximately 1 mm-2 mm.

From approximately 60° to 120° flexion and beyond, the contact on the lateral side moves further posteriorly, however the contact is still approximately 10 mm from a posterior edge of tibial component 14 to avoid damaging the edge. The contact between the femoral central groove 38 and the tibial ramp 58 is maintained in during the 60° to 120° flexion which results in the posterior displacement.

The lateral contact C7 moves posteriorly to the posterior portion 68 of the tibial component 14 at 120° flexion. The central contact is along the sloping ramp 58 during flexion at 120° as indicated by C8. On the medial side at 120° flexion and beyond, the contact C9 moves posteriorly 2 mm-4 mm to the posterior portion of the dished tibial surface 56. Due to the dishing of the medial tibial surface 56, at each angular position of flexion, the anterior and posterior stability of femoral component 12 on the medial tibial surface 56 is maintained.

In this one preferred embodiment, central groove 38 initially makes contact with ramp 58 at approximately 60° flexion as the posterior femoral displacement is preferably initiated at flexion angle of approximately 60°. As femoral component 12 flexes from 60° to maximum, the contact on the ramp 58 is towards the lower part of the ramp 58 to provide maximum stability.

The interaction between the ramp 58 and the femoral central groove 38 is such as to induce posterior displacement of the femoral component 12. However, because of the stability on the medial side, the motion is effectively a rotation of the femoral component about points on the medial side, so-called medial pivot motion. This resembles natural anatomic motion.

At 120 degrees flexion and beyond, the contact location of femoral component 14 on the lateral tibial bearing surface 54 is advantageously at least 8 mm and as much as approximately 10-12 mm from the posterior of the tibial component 14. The internal-external rotational laxity of the femur on the tibia is achievable without the femur contacting the extreme posterior edge of tibial component 1, 4 even at high angles of flexion. The rotational laxity is an important characteristic of anatomic knee motion.

Figures 10A, 10B:
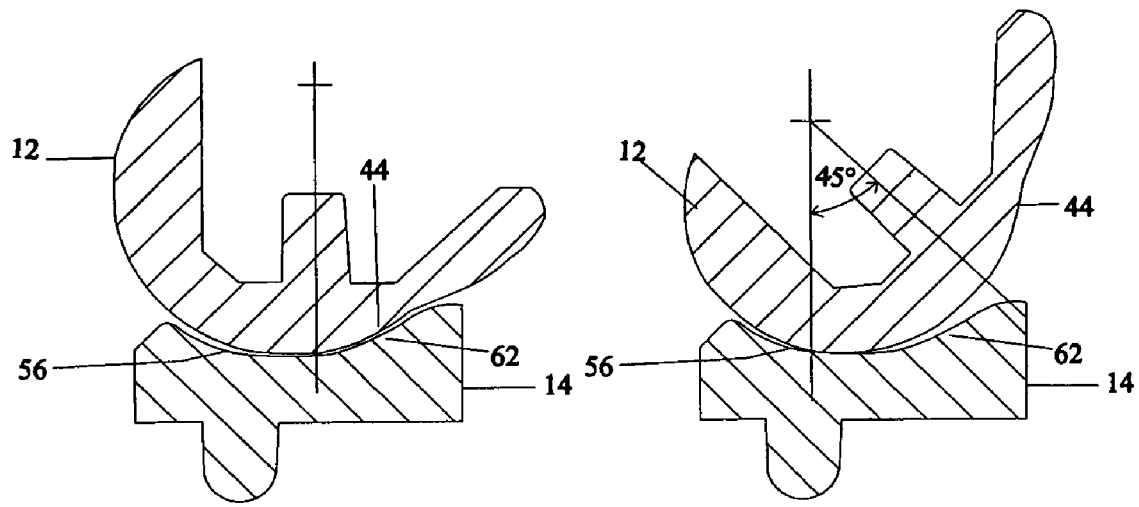
FIG. 10A shows a sectional view along plane-P that passes through the pad and recess in the anterior medial bearing surface of the femoral and tibial components of FIG. 1 at 0° flexion.
FIG. 10B shows a sectional view along plane-P that passes through the pad and recess in the anterior medial bearing surface of the femoral and tibial components of FIG. 1 at 45° flexion.

Referring to FIGS. 10A and 10B, the interaction of the recess 44 and pad 62 is described. The recess 44 and pad 62 fit together at 0° flexion. When femoral component 12 is flexed up to approximately 45°, for example, the medial condyle 34 articulates towards the steep pad 62, preventing or limiting the anterior translation of femoral component 12 on tibial component 14. The interaction of the pad 62 and recesses 44 prevents the femoral component 12 from skidding forward on the tibial component 14 during early flexion.

The edges of the recess 44 and pad 62 are advantageously rounded to avoid catching while the alignment of the knee is not exactly central as the knee is extended. The width of the recess 44 on the femoral component 12 is such that the recess 44 does not interfere with the region that the patella traverses on the patella flange 18. However, it is understood, that the medial recess 44 has sufficient space as the patella bearing area is less extensive on the medial side, in contrast to the lateral side where it is more extensive.

Figure 11:
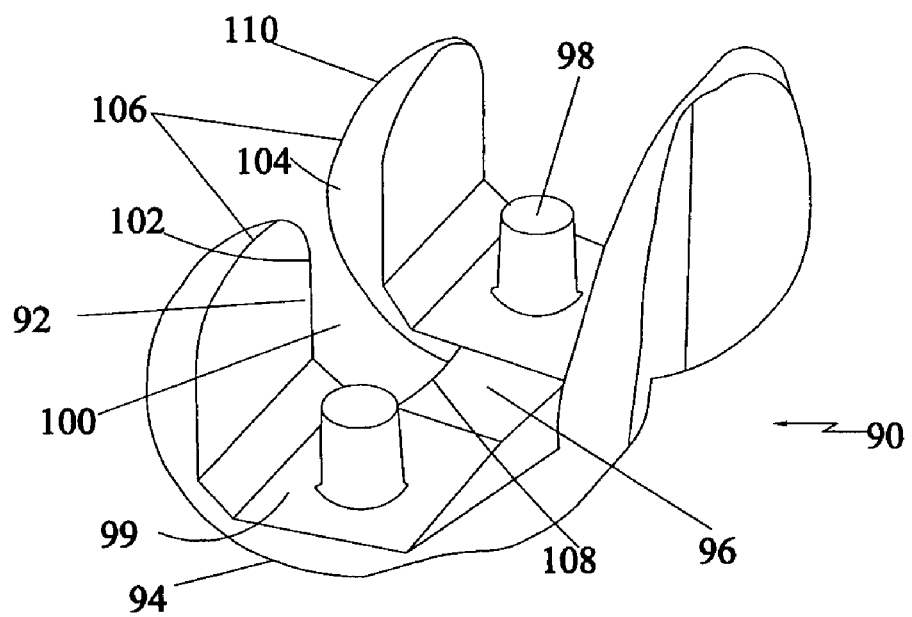
FIG. 11 shows a cruciate-retaining (CR) femoral component in accordance with the preferred embodiment of the present invention.

Referring to FIG. 11, in one more embodiment of the present invention, the PS femoral component 12 is replaced by a CR (cruciate retaining) femoral component 90. The CR femoral component 90 is approximately identical to the PS (posterior stabilized) femoral component 12 except for a central posterior portion 92. A distal portion 94 of the CR femoral component 90 includes a contoured and smooth platform 96 that is approximately centrally positioned between a pair of pegs 98 that are mounted in an interior portion 99 of the distal portion 94.

The CR femoral component 90 includes a central cutout 100 that is defined by smooth sides 102, 104 of the condyles 106, and side 108 of the platform 96. The sides 102, 104 and 108 are preferably smooth and rounded. In this preferred embodiment, the cutout 100 runs from the distal portion 94 towards the proximal posterior portion 110. The purpose of the cut-out is to provide free access of the posterior cruciate ligament. The posterior cutout or recess 66 on the tibial component similarly provides such access. It is, however, understood that the posterior displacement of the CR femoral component on the tibial component is now provided by the posterior cruciate ligament (PCL) while the medial pivotal rotation is still provided by the deeper and more dished medial tibial bearing surface 56 and shallower lateral tibial bearing surface 54.

In one another embodiment of the present invention, the tibial component 14 is mounted on a metal base plate. The base plate is fixed to the upper tibia such that the tibial component 14 rotatably flexes on the surface of the base plate, which is preferably called as a rotating platform design.

The femoral component 12 and the tibial component 14 of the knee joint are produced with known techniques in the art. It is, however, known in the art that smooth surfaces are preferably lofted from a multiplicity of frontal or sagittal plane sections. To generate this for the tibial surface, the outer surface of the geometrically defined femoral component 12 first positioned at zero degree flexion. The surface is then reproduced at a multiplicity of flexion angles. The position at each flexion angle is specified as being on the neutral path of motion resembling the motion of the anatomic knee.

The composite of the femoral positions at a full range of flexion up to, for example, in 135 degrees flexion is developed. The lower imprint of the composite of femoral surface is then made using a drape function to smooth the surface. The entire imprint is externally rotatable by approximately 5° relative to the tibia. This is done in order to reproduce the anatomic position of the femur on the tibia, when a symmetric tibial base plate is used. The required peripheral outline of the tibia is then superimposed on the imprint.

This peripheral outline is then treated as a 'cookie cutter' to cut a surface shape for the upper tibial surface. The surface is then extended downwards to create the tibial component 12. The resulting tibial surface advantageously accommodates all of the motions required between the femoral component 12 and the tibial component 14 in the neutral path of motion. The tibial receiving surface 28 is preferably manufactured exactly from the surface model itself using numerical methods. Approximations could be made to the surface using defined radii and solids to permit more traditional machining processes to be used.

Now referring to FIGS. 1 to 11, one advantage of the ramp 58 of the tibial component 14 is that the knee is foolproof to possible dislocation. Even in high flexion when there is considerable laxity in the joint 10 and high shear or varus-valgus moments are applied. The central groove 38 of the femoral component 12 could slide up the ramp 58 in such extreme conditions, but on relief of the forces, the femoral component 12 would simply slide back down the ramp 58 again to a stable position. The posterior displacement of the PS femoral component 12 on the tibial component 14 is obtained by the interaction between central groove 38 and central ramp 58.

The bearing receiving surface 28 advantageously receives and guides the position and motion of femoral component 12. The tibial bearing surfaces 54 and 56 are smooth and do not have corners or edges that can interact with the femoral component 12 and cause damage to the structure.

The provision of a medial femoral recess 46 and tibial pad 62 limits the anterior sliding of the femur on the tibia to advantageously avoid the paradoxical movements. The recess-pad arrangement increases the anterior conformity of the medial bearing surfaces 56 from 0°-60° flexion that limits the anterior displacement of the femoral component 12 on the tibial component 14 to limit paradoxical motion.

Posteriorly located cutout 66 on the tibial component 14 matches the shape of the upper tibia and allows access of the PCL. The groove 38 is shallow in the medial condyle 34 and lateral condyles 36 of posterior portion such that the depth is not reduced to a groove depth of zero to provide medial-lateral stability in high flexion.

In the preferred embodiment, the tibial receiving surface 28 has 5° of external rotation built in, that provides an anatomical position of the femur on the tibia at 0° flexion, preferably when a symmetric tibial base plate is used. Rounded edges of the femoral component 50 and 52 advantageously provide smooth sliding of soft tissues including muscle, tendon and capsular tissue, over the edges of the femoral component 12.

Large contact surface areas between the femoral components 12 or 90 and the tibial component 14 minimize wear and deformation of the polyethylene surfaces. Additionally, smooth contours of the central ramp 58 avoid stress concentrations and digging in at corners, which can result in damage to the plastic. The hump 24 is adapted to accommodate a distal portion of the groove 38.

An important feature of the present invention is that the tibial component 14 may be used with PS component 12 and with CR component 90. The knee joint 10 of the present invention requires only one tibial component 14 for either Cruciate Retaining femoral component 90 or Posterior Stabilized (PS) femoral component 12. Cutout 66 in the tibial component 14 allows the retained posterior cruciate ligament (PCL) to go through both recess/notch 44 and femoral cutout 66 when used with CR tibial component 90.

In the preceding specification, the invention has been described with reference to specific exemplary embodiments thereof. It will be evident, however, that various modifications, combinations and changes may be made thereto without departing from the broader spirit and scope of the invention as set forth in the claims that follow. It is understood that the present invention can combine one or more novel features of the different embodiments. The specification and drawings are accordingly to be regarded in an illustrative manner rather than a restrictive sense.

What is claimed is:

1. A prosthetic knee joint comprising:
a one-piece tibial component comprising a concave lateral bearing surface and a concave medial bearing surface separated by a central ramp characterized by a ramp height that decreases from anterior to posterior, said medial concave bearing surface being deeper than said lateral concave bearing surface, and further comprising a single raised pad spaced from the central ramp, located entirely within the concavity of the medial bearing surface, and completely surrounded by an anterior portion of said medial bearing surface;
a one-piece femoral component, in articulating contact with said tibial component, said femoral component comprising a patella flange, a lateral condylar surface, configured to engage said lateral bearing surface, and a medial condylar surface, configured to engage said medial bearing surface, said medial condylar surface comprising an antero-medially located recess, said recess operatively configured to engage said single raised pad during flexure of the knee joint; and
wherein said one-piece tibial component and said one-piece femoral component are operatively configured to provide flexion as well as internal-external rotation articulation.

2. The prosthetic knee joint in accordance with claim 1, wherein said one-piece femoral component comprises a central groove that passes between said lateral condylar surface and said medial condylar surface, said central groove configured to engage said central ramp during joint articulation.

3. The prosthetic knee joint in accordance with claim 2, wherein the depth of said central groove decreases as said central groove progresses from the proximal-anterior portion to the proximal-posterior portion of said femoral component.

4. The prosthetic knee joint in accordance with claim 2, wherein the medial condyle comprises said antero-medially located recess configured to articulate with said single raised pad and thereby limit the anterior sliding during flexion of said femoral component on the tibial component.

5. The prosthetic knee joint in accordance with claim 4, wherein said antero-medially located recess is configured to articulate with said single raised pad during early flexion thereby preventing said femoral component from skidding forward on said tibial component.

6. The prosthetic knee joint in accordance with claim 2, wherein said femoral component comprises a central slot in the posterior portion.

7. The prosthetic knee joint in accordance with claim 1, wherein said central ramp has a curved medial side and a lateral side that smoothly slopes toward the adjacent bearing surfaces.

8. The prosthetic knee joint in accordance with claim 1, wherein said central ramp is configured to guide said femoral component to displace posteriorly during flexion and displace anteriorly during extension.

9. The prosthetic knee joint in accordance with claim 1, wherein said single raised pad includes a posterior portion and an anterior portion, wherein an upper surface of said posterior portion of said single raised pad smoothly joins with said medial bearing surface at all points around said single raised pad's periphery.

10. The prosthetic knee joint in accordance with claim 9, wherein a sagittal profile of said upper surface of said single raised pad has a smaller radius than said medial bearing surface adjacent to said single raised pad.

11. The prosthetic knee joint in accordance with claim 1, wherein said tibial component comprises a cutout that is positioned centrally in the posterior portion of said tibial component, and posterior portion of said central ramp smoothly and gradually meets with said cutout.

* * * * *